(12) United States Patent
Van Den Brink et al.

(10) Patent No.: US 11,224,496 B2
(45) Date of Patent: Jan. 18, 2022

(54) AUTOMATIC SENSOR IDENTIFICATION

(71) Applicant: KONINKLIJKE PHILIPS N.V., Eindhoven (NL)

(72) Inventors: Hendrikus Bernardus Van Den Brink, Eindhoven (NL); Ruud Van Dijk, Best (NL); Frans Henk Kremer, Eindhoven (NL); Kasper Gerard Van Wouw, Veldhoven (NL); Ivo Don Stuyfzand, Eindhoven (NL)

(73) Assignee: KONINKLIJKE PHILIPS N.V.

( * ) Notice: Subject to any disclaimer, the term of this patent is extended or adjusted under 35 U.S.C. 154(b) by 300 days.

(21) Appl. No.: 15/762,148

(22) PCT Filed: Sep. 23, 2016

(86) PCT No.: PCT/EP2016/072765
§ 371 (c)(1),
(2) Date: Mar. 22, 2018

(87) PCT Pub. No.: WO2017/051010
PCT Pub. Date: Mar. 30, 2017

(65) Prior Publication Data
US 2018/0289447 A1 Oct. 11, 2018

(30) Foreign Application Priority Data

Sep. 24, 2015 (EP) ..................... 15186708

(51) Int. Cl.
*A61B 5/02* (2006.01)
*A61B 90/94* (2016.01)
(Continued)

(52) U.S. Cl.
CPC ............... *A61B 90/94* (2016.02); *A61B 1/31* (2013.01); *A61B 5/0002* (2013.01); *A61B 5/01* (2013.01);
(Continued)

(58) Field of Classification Search
CPC ... A61B 5/02; A61B 5/02007; A61B 5/02021; A61B 5/02028; A61B 5/02035;
(Continued)

(56) References Cited

U.S. PATENT DOCUMENTS

| 4,856,530 A | * | 8/1989 | Vandervelden | ........ | A61B 5/028 600/505 |
| 6,684,101 B2 | * | 1/2004 | Daum | ................ | A61N 1/36521 600/483 |

(Continued)

FOREIGN PATENT DOCUMENTS

| DE | 10337235 A1 | 3/2005 |
| EP | 0171073 A1 | 2/1986 |

(Continued)

OTHER PUBLICATIONS

Vandahl, T. et al "New SAW-Sensor-Device with Identification capability", IEEE Ultrasonics Symposium, 1995.

(Continued)

*Primary Examiner* — Ahmed M Farah

(57) ABSTRACT

The present invention relates to patient monitoring, such as hemodynamic monitoring. In order to perform provide monitoring in various scenarios, a patient monitoring device (10) is provided that comprises a patient medical monitoring unit (12) and an information unit (14). The patient medical monitoring unit is configured to perform monitoring at least one physiological parameter of a patient. The information unit is configured to provide a data carrier signal (16) indicative of information about the patient medical monitoring unit, for example, upon connection to a monitoring system. The data carrier signal is provided as an analogue sequence (18) comprising a predetermined waveform (20) indicative of the information about the patient medical monitoring unit.

18 Claims, 2 Drawing Sheets

(51) Int. Cl.

| | |
|---|---|
| *A61B 5/0205* | (2006.01) |
| *A61B 90/98* | (2016.01) |
| *A61B 5/00* | (2006.01) |
| *G06F 9/445* | (2018.01) |
| *A61B 5/24* | (2021.01) |
| *A61B 5/318* | (2021.01) |
| *A61B 1/31* | (2006.01) |
| *A61B 5/01* | (2006.01) |
| *A61B 5/029* | (2006.01) |
| *A61B 5/0215* | (2006.01) |
| *A61B 5/027* | (2006.01) |
| *A61B 5/024* | (2006.01) |
| *A61B 5/107* | (2006.01) |
| *A61B 5/145* | (2006.01) |

(52) U.S. Cl.
CPC .............. *A61B 5/02* (2013.01); *A61B 5/0205* (2013.01); *A61B 5/02007* (2013.01); *A61B 5/029* (2013.01); *A61B 5/02035* (2013.01); *A61B 5/02055* (2013.01); *A61B 5/24* (2021.01); *A61B 5/318* (2021.01); *A61B 5/7232* (2013.01); *A61B 5/7264* (2013.01); *A61B 90/98* (2016.02); *G06F 9/445* (2013.01); *G06F 9/44521* (2013.01); *A61B 5/0022* (2013.01); *A61B 5/0024* (2013.01); *A61B 5/0084* (2013.01); *A61B 5/024* (2013.01); *A61B 5/027* (2013.01); *A61B 5/0215* (2013.01); *A61B 5/107* (2013.01); *A61B 5/14507* (2013.01); *A61B 2503/40* (2013.01); *A61B 2560/0223* (2013.01); *A61B 2560/0242* (2013.01); *A61B 2560/0443* (2013.01); *A61B 2560/0475* (2013.01); *A61B 2562/0219* (2013.01); *A61B 2562/06* (2013.01); *A61B 2562/085* (2013.01); *A61B 2562/226* (2013.01)

(58) Field of Classification Search
CPC ... A61B 5/0205; A61B 5/021; A61B 5/02108; A61B 5/02116; A61B 5/02125; A61B 5/0215; A61B 5/02152; A61B 5/024; A61B 5/02405; A61B 5/0255; A61B 5/026; A61B 5/027; A61B 5/029; A61B 5/72; A61B 5/7225; A61B 5/7232; A61B 5/7235; A61B 5/7264; A61B 90/90; A61B 90/94; A61B 90/96; A61B 90/98; A61B 2560/04; A61B 2560/0475; A61B 2560/0487; A61B 5/0245

USPC ....... 600/301, 309, 368, 437, 438, 481–488, 600/500, 505, 508, 509
See application file for complete search history.

(56) References Cited

U.S. PATENT DOCUMENTS

| | | | |
|---|---|---|---|
| 7,618,369 B2 * | 11/2009 | Hayter | A61B 5/14532 600/309 |
| 8,509,882 B2 * | 8/2013 | Albert | A61B 5/02416 600/509 |
| 2006/0229506 A1 * | 10/2006 | Castellanos | A61B 5/14551 600/300 |
| 2006/0248398 A1 * | 11/2006 | Neel | G16H 40/63 714/33 |
| 2007/0032246 A1 * | 2/2007 | Feher | A61B 5/0022 455/456.1 |
| 2007/0204802 A1 | 9/2007 | Davies | |
| 2007/0273504 A1 * | 11/2007 | Tran | A61B 5/742 340/539.12 |
| 2009/0156908 A1 * | 6/2009 | Belalcazar | A61B 5/287 600/301 |
| 2011/0027009 A1 | 2/2011 | Kusiak et al. | |
| 2011/0319779 A1 * | 12/2011 | Sweeney | A61B 5/026 600/515 |
| 2012/0029311 A1 * | 2/2012 | Raptis | G16H 10/60 600/301 |
| 2013/0178727 A1 * | 7/2013 | Hayter | A61B 5/14546 600/365 |
| 2013/0190633 A1 | 7/2013 | Dorando | |
| 2013/0262730 A1 | 10/2013 | Al-Ali | |
| 2014/0194866 A1 | 7/2014 | Wang | |
| 2015/0151142 A1 * | 6/2015 | Tyler | A61B 8/4477 601/2 |
| 2018/0228386 A1 * | 8/2018 | McCall | A61B 5/02156 |

FOREIGN PATENT DOCUMENTS

| | | |
|---|---|---|
| EP | 1834580 A1 | 9/2007 |
| JP | 2002010983 A | 1/2002 |
| JP | 2005114697 A | 4/2005 |
| JP | 2005261628 A | 9/2005 |

OTHER PUBLICATIONS

"Labpro Technical Reference Manual", Feb. 2002, pp. 1-96.
Mark, John et al "The IEEE 1451.4 Standard for Smart Transducers", IEEE Strandards Association, Jul. 1, 2004, pp. 1-14, XP055528479.

* cited by examiner

AUTOMATIC SENSOR IDENTIFICATION

CROSS-REFERENCE TO PRIOR APPLICATIONS

This application is the U.S. National Phase application under 35 U.S.C. § 371 of International Application No. PCT/EP2016/072765, filed on Sep. 23, 2016, which claims the benefit of European Patent Application No. 15186708.2, filed on Sep. 24, 2015. These applications are hereby incorporated by reference herein.

FIELD OF THE INVENTION

The present invention relates to patient monitoring and in particular to a patient monitoring device, to a patient monitoring system, to a method for operating a patient monitoring system, to a computer program element, and to a computer-readable medium.

BACKGROUND OF THE INVENTION

Patient monitoring, such as hemodynamic monitoring relates to the observation of static and functional (hemodynamic) parameters over time, such as blood pressure and heart rate. The patient related medical parameters may be used, e.g., to provide clinical information that may impact medical decision-making. In order to determine for example hemodynamic parameters, a patient monitoring device may be provided, which is capable of providing hemodynamic data and information, e.g. on a continuing basis and in real-time. The hemodynamic monitoring devices may be connected to a hemodynamic monitoring system, e.g. for further processing and displaying the measurements. A hemodynamic monitoring system may be customized to connect different hemodynamic monitoring devices and to provide diverse functionalities, e.g. dependent on the hemodynamic situation a medical doctor tries to solve, or on the institution and the country where a medical doctor is practicing. For example, US 2011/0270091 A1 describes a catheter-based ultrasound imaging system.

SUMMARY OF THE INVENTION

There may be a need to provide a patient monitoring system for better adapting to various scenarios.

The object of the present invention is solved by the subject-matter of the independent claims, wherein further embodiments are incorporated in the dependent claims. It should be noted that the following described aspects of the invention apply also for the patient monitoring device, for the patient monitoring system, for the method for operating a patient monitoring system, for the computer program element, and for the computer-readable medium.

According to a first aspect of the present invention, a patient monitoring device is provided that comprises a patient medical monitoring unit and an information unit. The patient medical monitoring unit is configured to perform monitoring at least one physiological parameter of a patient. The information unit is configured to provide a data carrier signal indicative of information about the patient medical monitoring unit. The data carrier signal is provided as an analogue sequence comprising a predetermined waveform indicative of the information about the patient medical monitoring unit. The information comprises at least one of the group of: serial number, batch number, production data, and calibration parameters. The information comprises at least one of the group of: serial number, batch number, production data, and calibration parameters.

It is noted that in the following, aspects are discussed in relation with a hemodynamic monitoring device as an example for the patient monitoring device. It is noted that these aspects are also provided in relation with other types of patient monitoring devices, which are described below, although this is not explicitly mentioned when discussing the particular aspects.

For example, a hemodynamic monitoring device is provided that comprises a hemodynamic monitoring unit and an information unit. The hemodynamic monitoring unit is configured to perform hemodynamic monitoring. The information unit is configured to provide a data carrier signal indicative of information about the hemodynamic monitoring unit. The data carrier signal is provided as an analogue sequence comprising a predetermined waveform indicative of the information about the hemodynamic monitoring unit.

Advantageously, the information about the hemodynamic monitoring device, such as serial number, batch number or calibration parameters, can be transmitted to a hemodynamic monitoring system. The hemodynamic monitoring system may collect the information and consider it for further steps, for example, to enable certain functionalities to meet the hemodynamic situation a medical doctor tries to solve or to increase the customer's value by integrating new functionalities. Further, unlike a remote-readable identification tag (e.g. radio-frequency identification (RFID)), no interrogators or readers, i.e. two-way radio transmitter-receivers, are required to send a signal to an RFID tag and read its response. The information unit of the hemodynamic monitoring device can provide (or actively generate) the information upon connection to the hemodynamic monitoring system without any additional interrogators or readers. Certain information may be factory-assigned like serial number. Other information may relate to situation-specific parameters, such as department information. A system user may also add further object-specific information, e.g. by writing it into a memory element.

Furthermore, the data carrier signal in form of an analogue sequence makes it possible to transmit the information over an analogue interface, which may also be used to support the transmission of analogue data collected from certain, e.g. hemodynamic monitoring devices including, for example, a Doppler ultrasound sensor, a venous pressure sensor, etc. The predetermined waveform may comprise the information of e.g. serial number, batch number, production data, calibration parameters, etc.

According to an example, the information unit sends data upon connection to a patient monitoring system, such as a hemodynamic monitoring system.

Advantageously, the information data is a part of the measured data (e.g. blood pressure or heart rate). They may share the same signal paths. For example, both hemodynamic measurement data and information data may be transmitted over cables, which may avoid interferences as experienced between the two paths of the reader and identifier of RFID tags. In a further example, the hemodynamic monitoring system may also provide an external power source for the hemodynamic monitoring device via cables.

According to an example, the patient medical monitoring unit comprises at least one sensor for monitoring the at least one physiological parameter. Further, the at least one sensor is provided at an interventional device. The interventional device relates to at least one of the group of:

flexible elongate object to be inserted in a cavity or lumen of an anatomic structure; and rigid or flexible elongate object to be penetrated at least a part of an anatomic structure.

For example, the flexible elongate object for insertion may be a catheter. For example, the flexible elongate object for penetration may be a biopsy device, such as a biopsy needle.

According to an example, the patient medical monitoring unit is provided as at least one of the group of:
i) a hemodynamic monitoring unit providing at least one physiological parameter of the patient of the group of: blood pressure, blood volume, blood flow, blood flow speed, blood consistency, blood oxygenation, elasticity of a vessel, and geometry of a vessel;
ii) a cardiac monitoring unit providing at least one cardiac related parameter of the patient of the group of: heart rate, cardiac index, cardiac electric activity;
iii) a gastroenterological monitoring unit providing at least one parameter of the patient of the group of: images inside cavities of an intestinal tract, chemical consistence of content inside a cavity of the intestinal tract, and temperature; and
iv) a neurological monitoring unit providing a signal indicative of a neurological electric activity of the patient.

The term "providing" relates to measuring the parameter with a respective sensor. In case of images, the term "providing" relates to generating image data.

According to an example, the patient medical monitoring unit is provided as a catheter insertable into a vessel structure of a patient and provided as:
i) hemodynamic monitoring unit measuring at least one physiological parameter of the patient of the group of: blood pressure, blood volume, blood flow, blood flow speed, blood consistency, blood oxygenation, elasticity of a vessel, and geometry of a vessel; and/or
ii) cardiac monitoring unit measuring at least one cardiac related parameter of the patient of the group of: heart rate, and cardiac index.

For example, the catheter may be a pressure wire for FFR measuring.

According to a second aspect of the present invention, a patient monitoring system is provided that comprises an interface device, a data processing device, and a patient monitoring device according to one of the examples described above and in the following. The patient monitoring device is configured to provide a data carrier signal. The interface device is configured to receive the data carrier signal and to provide the received data carrier signal to the data processing device. The data processing device is configured to identify the information about the patient monitoring device based on the received data carrier signal and to consider the identified information for further steps.

For example, a hemodynamic monitoring system is provided that comprises an interface device, a data processing device, and a hemodynamic monitoring device according to one of the examples described above and in the following. The hemodynamic monitoring device is configured to provide a data carrier signal. The interface device is configured to receive the data carrier signal and to provide the received data carrier signal to the data processing device. The data processing device is configured to identify the information about the hemodynamic monitoring device based on the received data carrier signal and to consider the identified information for further steps.

Advantageously, the hemodynamic monitoring system can adapt to various scenarios based on the identified information about the hemodynamic monitoring device. For example, the hemodynamic monitoring system may unlock extra functionalities (e.g. fractional flow reserve (FFR)) if the manufacturer of the device is an authorized vendor and/or the hemodynamic monitoring device has an authorized geographic region of use. In a further example, the hemodynamic monitoring system may allow measurement of a further kind of parameter (e.g. flow, viscosity of blood) over an interface that is normally used for e.g. pressure. Upon detection of the information and identification of a further kind of parameter, the hemodynamic monitoring system may treat the signal e.g. on the pressure input port as a different signal (e.g. flow of blood). In other words, it is possible to use a standard input port (e.g. pressure input port) to measure a new parameter that may not have a dedicated input port. Thus, a hemodynamic monitoring system can adapt to be connected to one or more new hemodynamic monitoring devices without adding further dedicated input ports. A simple and flexible hemodynamic monitoring system may thus be achieved.

According to an example, the data processing device is configured to detect the predetermined waveform of the analogue sequence of the received data carrier signal, and to identify the information about the patient monitoring device, e.g. the hemodynamic monitoring device, based on the detected predetermined waveform.

Advantageously, the information about the patient monitoring device, such as serial number or code of geographic regions of use, may be identified and considered for further steps, for example, whether or not to enable certain functions, or whether or not to perform measurements of new parameters using a standard input port of the patient monitoring system.

According to an example, the data processing unit is configured to enable or disable at least one locked functionality of the patient monitoring system based on the identified information.

Advantageously, many features of the patient monitoring systems, such as hemodynamic monitoring systems, may be customized e.g. to each cath lab's needs without any further hardware changes. For example, the functionality of this input port (or channel) may be extended, such as by switching on FFR or instant wave-free ratio (iFR), or even performing a completely new measurement like viscosity of blood.

According to an example, a secondary monitoring unit is provided that provides an analogue signal that is used as a carrier signal. The information unit belongs to the secondary monitoring unit. Further, the information unit is configured to add the data carrier signal indicative of information about the patient medical monitoring unit to the carrier signal.

According to an example, the at least one locked functionality comprises at least one of the group of: FFR, pressure measurement, iFR, and new functionality comprising flow, oxygenation and viscosity.

According to a third aspect of the present invention, a method for operating a patient monitoring system is provided. The method comprises the following steps:
(a) providing a data carrier signal indicative of information about the patient monitoring device upon connecting the patient monitoring device to a patient monitoring system;
(b) receiving the data carrier signal and identifying the information about the patient monitoring device based on the received data carrier signal; and
(c) considering the identified information for further steps.

The data carrier signal is provided as an analogue sequence comprising a predetermined waveform indicative of the information about the hemodynamic monitoring device. The information comprises at least one of the group of: serial number, batch number, production data, and calibration parameters.

In an example, the method is a method for operating a hemodynamic monitoring system. The method comprises the following steps:
(a) providing a data carrier signal indicative of information about the hemodynamic monitoring device upon connecting the hemodynamic monitoring device to a hemodynamic monitoring system;
(b) receiving the data carrier signal and identifying the information about the hemodynamic monitoring device based on the received data carrier signal; and
(c) considering the identified information for further steps.

The data carrier signal is provided as an analogue sequence comprising a predetermined waveform indicative of the information about a patient medical monitoring unit.

The term "considering" relates to using the information about the hemodynamic monitoring device to make a choice or decision how to proceed further.

According to an example, the method further comprises:
(d) detecting the predetermined waveform of the analogue sequence of the received data carrier signal, and identifying the information about the patient monitoring device based on the detected predetermined waveform.

According to an example, the method further comprises:
(e) enabling or disabling at least one locked functionality of the patient monitoring system based on the identified information about the patient monitoring device.

According to an aspect, a monitoring device such as a hemodynamic monitoring device (or an input device) is provided that generates a specific analogue input sequence, such as a waveform, upon connection to a hemodynamic monitoring system. The specific analogue input sequence may be identified by the hemodynamic monitoring system. When the specific analogue input sequence is detected, the hemodynamic monitoring system may unlock certain extra functionality. For example, on the hemodynamic monitoring device side, the hemodynamic monitoring device may generate a certain specific analogue signal sequence. This sequence may be generated when the device is powered, or upon a user action, such as by pushing a "connect" button. On the hemodynamic monitoring system side, a sub-system may detect the input, and enable certain extra functionality upon detection of the certain specific analogue signal sequence. The sub-system may be either implemented in hardware and/or software. The extra functionality may comprise FFR, pressure measurement, and IFR. This allows a hemodynamic monitoring system to provide functionalities based on the information about the hemodynamic monitoring devices for better adapting to e.g. the hemodynamic situation a medical doctor tries to solve. Furthermore, it may be used to transmit a signal, for which the hemodynamic monitoring system does not have an input port. For example, the analogue pressure input ports of a hemodynamic monitoring system may be used for measuring parameters, for which no catheters and dedicated input ports exists, like flow, oxygenation of blood, viscosity of blood. By transmitting and detecting the specific analogue sequence, an input port that is usually a pressure input port may be used for detecting new parameters without the need for manual configuration. This makes it possible to include new functionalities, for example, measuring new parameters like flow, viscosity of blood, without the need of adding new input ports or changing the hardware. In other words, the hemodynamic monitoring system may be connected to a hemodynamic monitoring device even if no dedicated input port (channel) exists for such a hemodynamic monitoring device. This may simplify the design of the hemodynamic monitoring system.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
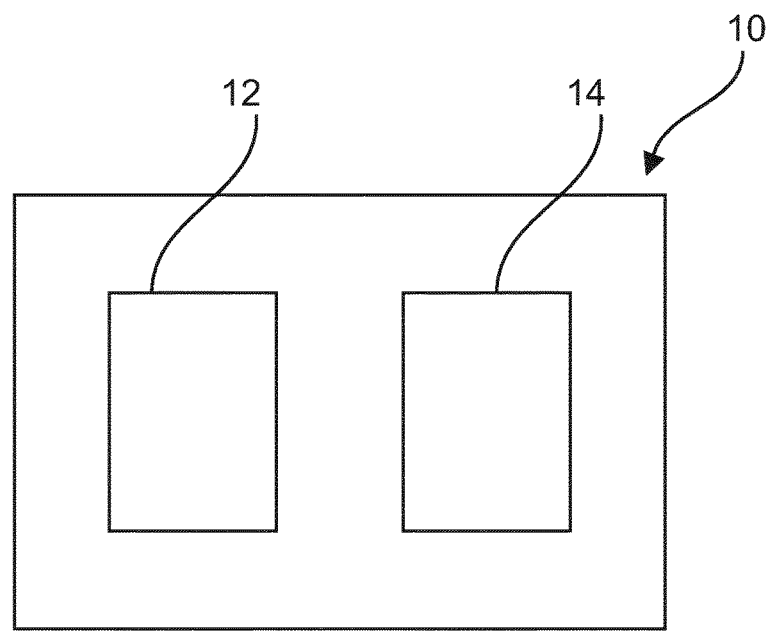
FIG. 1 shows an example of a hemodynamic monitoring device in a schematic view.

FIG. 1 shows an example of a patient monitoring device 10 that comprises a patient medical monitoring unit 12 and an information unit 14. For example, the patient monitoring device 10 is a hemodynamic monitoring device. For example, the patient medical monitoring unit 12 is a hemodynamic monitoring unit. The patient medical monitoring unit 12 is configured to perform monitoring at least one physiological parameter of a patient, such as hemodynamic monitoring. The information unit 14 is configured to provide a data carrier signal 16 (see an example in FIG. 2) indicative of information about the patient medical monitoring unit.

It is noted that in the following description, aspects are discussed for the embodiments in relation with a hemodynamic monitoring device as an example for the patient monitoring device. It is noted that these aspects are also provided in relation with other types of patient monitoring devices, which are described below, although this is not explicitly mentioned when discussing the particular aspects.

The term "hemodynamic monitoring" relates to collection and analysis of qualitative and quantitative data of cardiopulmonary function. This monitoring may include the use of electrical, photometric, pressure transducing, and other non-invasive devices, as well as the application of a number of intravascular catheters. For example, fluid-filled monitoring systems attach to intravascular catheters and are used for continuous invasive measurement of arterial and cardiac pressures.

The term "hemodynamic monitoring device", also referred to as "input device", relates to a device that measures and monitors cardiopulmonary function. This may include, for example, electrical, photometric, pressure transducing, and other non-invasive devices, as well as a number of intravascular catheter, e.g. for providing IVUS (intravascular ultrasound), FFR, OCT (optical coherence tomography) and other intravascular modalities. The term "hemodynamic monitoring device" may also relate to a multi-measurement device that may provide the measurements of e.g. ECG (electrocardiography), respiration, SpO2 (pulse oximetry), and non-invasive blood pressure.

For example, not shown in detail, the patient medical monitoring unit comprises at least one sensor for monitoring the at least one physiological parameter. The at least one sensor is provided at an interventional device, and the interventional device relates to at least one of the group of: flexible elongate object to be inserted in a cavity or lumen of an anatomic structure, and rigid or flexible elongate object to be penetrate at least a part of an anatomic structure.

For example, the patient medical monitoring unit is provided as at least one of the group of:
i) a hemodynamic monitoring unit providing at least one physiological parameter of the patient of the group of: blood pressure, blood volume, blood flow, blood flow speed, blood consistency, elasticity of a vessel, and geometry of a vessel;
ii) a cardiac monitoring unit providing at least one cardiac related parameter of the patient of the group of: heart rate, cardiac index, cardiac electric activity;
iii) a gastroenterological monitoring unit providing at least one parameter of the patient of the group of: images inside cavities of an intestinal tract, chemical consistence of content inside a cavity of the intestinal tract, and temperature; and
iv) a neurological monitoring unit providing a signal indicative of a neurological electric activity of the patient.

For example, also not shown in detail, the patient medical monitoring unit is provided as a catheter insertable into a vessel structure of a patient and provided as:
i) hemodynamic monitoring unit measuring at least one physiological parameter of the patient of the group of: blood pressure, blood volume, blood flow, blood flow speed, blood consistency, elasticity of a vessel, and geometry of a vessel; and/or
ii) cardiac monitoring unit measuring at least one cardiac related parameter of the patient of the group of: heart rate, and cardiac index.

The term "hemodynamic monitoring system" relates to a system provided to measure and monitor cardiopulmonary function. Besides the actual hemodynamic monitoring devices, the system may comprise further components such as data processing unit(s), storage devices, displays and other types of data interfaces.

The term "hemodynamic monitoring unit", relates to the sensing part of a hemodynamic monitoring device, such as sensors for central venous pressure measurement, arterial pressure measurement, and airway pressure measurement. A hemodynamic monitoring device may have several hemodynamic monitoring units for performing so-called multi-measurements, i.e. measuring several hemodynamic parameters at the same time with several hemodynamic monitoring units, for example a combination of ECG, Respiration, SpO2, and/or non-invasive blood pressure measurements.

The term "information unit", also referred to as "information providing unit", relates to an electronic component, such as a signal generator IC (integrated circuit), which generates a data carrier signal, for example, in form of electrical waveforms over a certain range of frequencies carrying the information about the hemodynamic monitoring device. Hence, the information unit may also be referred to as "signal generating unit" or as "signal generator". The information unit 14 may comprise a memory element, such as a read-only memory (ROM) circuit, in which the information is stored. The information may be read-only, such as a factory-assigned serial number, or may be read/write, where the information data can be written into the memory element or amended by a user.

The term "information about the hemodynamic monitoring device" may relate to identifying information about the hemodynamic monitoring device, such as a unique tag serial number. The information may also be product-related information such as a stock number, lot or batch number, production date, or other specific information like calibration parameters that are needed for processing signals.

The term "data carrier signal", also referred to as "encoded signal", relates to a signal modulated or encoded to carry data. The data carrier signal comprises, i.e., is modulated with, information data (e.g. serial number) that is uniquely assigned to the particular hemodynamic monitoring device. For example, the information unit 14 may convert the information data stored in the memory element, i.e. a digital stream, into data carrier signal.

The data carrier signal may be provided in several ways. For example, the data carrier signal may be provided or generated when the hemodynamic monitoring device is powered, for example, upon connection to a hemodynamic monitoring system, which provides an external power source for the hemodynamic monitoring device. In a further example, the data carrier signal may be generated upon a user action, for example, by pushing a "connect" button.

In this way, a hemodynamic monitoring system may advantageously collect the information about the connected hemodynamic monitoring device, such as the manufacturer or geographic region of use, and then determine the further steps based on the information, for example, to unlock further extra functionalities if the device has an authorized manufacturer and an authorized geographic region of use. The information may also enable the hemodynamic monitoring system to adapt a standard input port e.g. for pressure for measuring new parameters like flow of blood, and to display the measurement results of the new parameters to a user, e.g. a medical doctor or a nurse.

Figure 2:
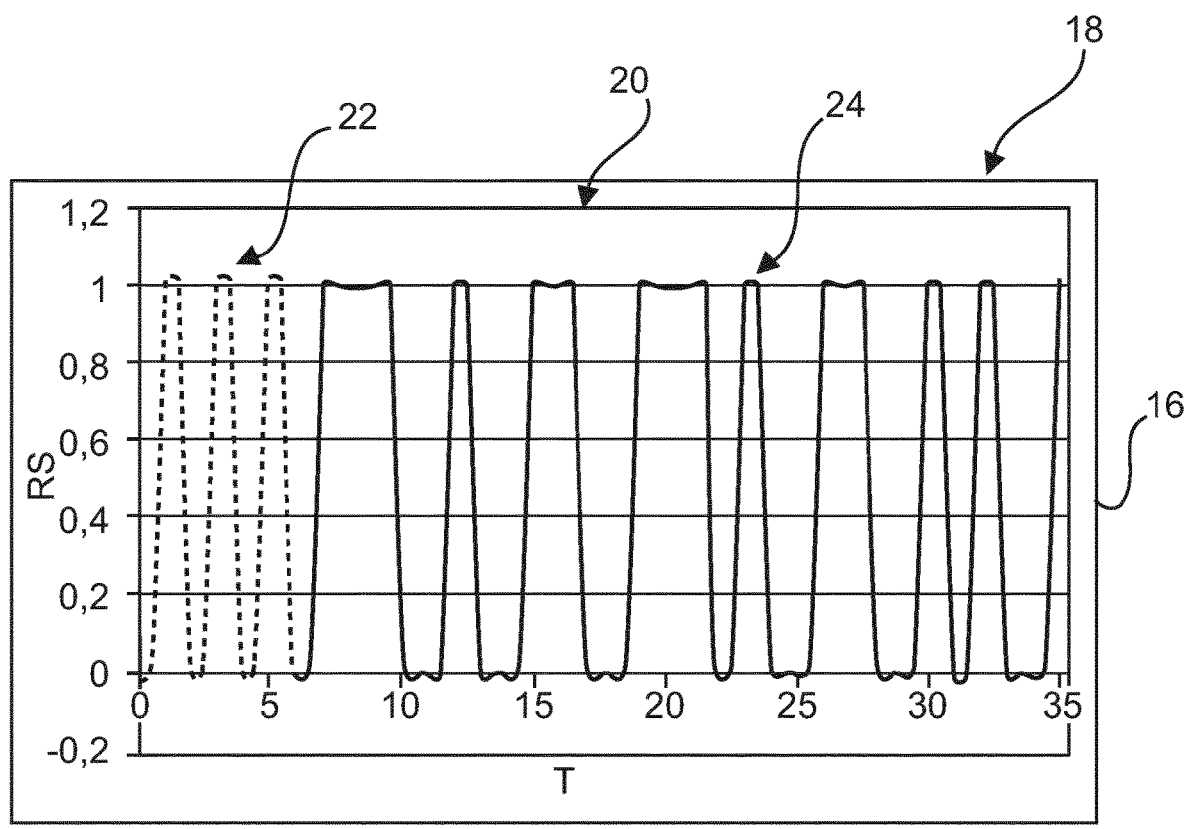
FIG. 2 shows an example of a data carrier signal.

FIG. 2 shows an example of the data carrier signal 16 provided as an analogue sequence 18 comprising a predetermined waveform 20 indicative of the information about the hemodynamic monitoring unit 12.

The horizontal axis in FIG. 2 represents time (T) in an arbitrary unit, and the vertical axis indicates a relative signal (RS) in an arbitrary unit.

The interface between a hemodynamic monitoring device and a hemodynamic monitoring system may be analogue to support the transmission of analogue data, such as the data collected by a Doppler ultrasound sensor or a venous pressure sensor. Thus, the data carrier signal in form of an analogue sequence makes it possible to transmit the information over such an analogue interface.

Also shown in FIG. 2 as an option, the predetermined wave 20 may comprise two parts: a fixed part 22 (indicated by a dashed line) and a variable part 24 (indicated by a solid line). The fixed part 22, which is also referred to as "tag waveform", "marker waveform", or "intro period", is used to differentiate the data carrier signal from the usual measurement signal and to indicate the location of the variable part 24 that contains the information like serial number, batch number and calibration parameters. Hence, the variable part 24 may also be referred to as "information waveform". For example, as shown in FIG. 2, the fixed part 22 starts with a fixed pulse sequence 010101, indicating the beginning of the tag or marker, followed by a waveform transmitting the actual data, i.e. the information waveform as the variable part 24.

It is also noted that the analogue sequence in FIG. 2 is merely for illustration purposes. The fixed part 22 may be provided as any suitable waveform. The information data, e.g. serial number, batch number, and other specific information like calibration parameters, may be modulated, i.e. converted to the variable part 24, in various ways, e.g., amplitude modulation (AM), frequency shift keyed (FSK) modulation or phase shift keyed (PSK) modulation, and the like. If desired, the analogue sequence 18 may comprise a plurality of the fixed parts 22 arranged to indicate the locations of several pieces of information data about the hemodynamic monitoring device. Further, a piece of information data, such as the serial number, may comprise two tag waveforms: one indicating the beginning, and the other indicating the ending. The tag waveform that indicates the beginning of the information may also be referred to as beginning tag waveform; and the tag waveform that indicates the ending of the information may also be referred to as ending tag waveform.

In a further example, the information unit 14 sends data upon connection to a hemodynamic monitoring system (not further shown). Besides the analogue sequence 18, the data may further comprise other measured hemodynamic parameters, such as blood pressure or ECG, which are provided to the hemodynamic monitoring system.

Figure 3:
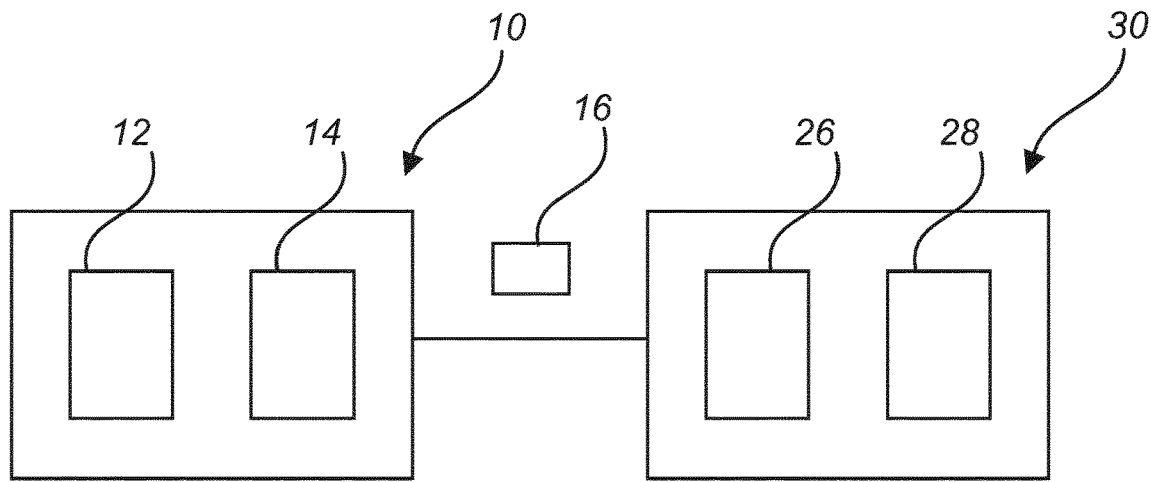
FIG. 3 shows an example of a hemodynamic monitoring system in a schematic view.

FIG. 3 shows an example of a patient monitoring system 30, e.g. a hemodynamic monitoring system. The patient monitoring system 30 comprises an interface device 26, a data processing device 28, and the patient monitoring device 10 according to one of the above-mentioned examples. The patient monitoring device 10 is configured to provide a data carrier signal 16, for example, upon connection to the patient monitoring system 30 via the interface device 26. The interface device is configured to receive the data carrier signal and to provide the received data carrier signal 16 to the data processing device 28. The data processing device 28 is configured to identify the information about the patient monitoring device 10 based on the received data carrier signal 16 and to consider the identified information for further steps.

The term "interface device" relates to a device that facilitates the data communication between one or more hemodynamic monitoring devices and the hemodynamic monitoring system. In an example, a hemodynamic monitoring device, such as a pressure sensor, may be part of the interface device. In a further example, a hemodynamic monitoring device may be a separate component, and may be connected to the interface device e.g. via cables. In a still further example, the interface device may comprise one or more processing units for analyzing, interpreting, and presenting hemodynamic data. Hence, this type of interface devices may also be referred to as hemodynamic monitoring system, such as Philips Xper Flex Cardio physiomonitoring system.

In an example, the data processing device 28 is configured to detect the predetermined waveform 20 (see an example in FIG. 2) of the analogue sequence 18 of the received data carrier signal, and to identify the information about the patient monitoring device based on the detected predetermined waveform.

The information about the patient monitoring device may be identified, e.g. by comparing the received data carrier signal to the tag (or marker) waveform, e.g. the fixed part 24 in FIG. 2. After detection of the tag waveform, the data processing unit may switch mode to receiving the data from the waveform, e.g. the variable part 24 in FIG. 2 that contains the information about the patient monitoring device. Detecting the tag waveform may be done in various ways. For example, the number of up- and down-going flanks, the amplitudes, and the time distance of the analogue sequence may be counted to identify the tag waveform. After the tag waveform (or intro period), the data processing unit may determine the position, direction, and size of the up- and down-going flanks of the information waveform and covert the information waveform into received bits (or a digital bit stream). After a predetermined ending tag waveform, the data processing unit may switch back to normal mode.

Other methods for identifying the information about the patient monitoring devices will also be appreciated. For example, the interface device 26 may further comprise a memory unit (not further shown) that stores the tag waveform as a reference waveform. The data processing device may compare the received data carrier signal and the stored reference waveform to identify the tag waveform. Likewise, the information waveform followed after the beginning tag waveform may be converted to a digital bit stream by any suitable demodulation and decoding methods (depending on the modulation methods).

In a further example, the data processing device 28 is configured to enable or disable at least one locked functionality of the patient monitoring system based on the identified information.

The term "locked functionality" means that certain functionalities of the patient monitoring system are disabled e.g. to prevent unauthorized usage, unless the patient monitoring device has an authorized identity, for example, an authorized manufacturer, or an authorized geographic region of use.

The term "to enable", also referred to as "to unlock", relates to permitting usage of certain "locked" functionality when the patient monitoring device has an authorized identification, for example, an authorized serial number, batch number, and/or calibration parameters.

Likewise, the term "to disable", also referred to as "to lock", relates to preventing usage of certain "locked" functionality when the patient monitoring device does not have an authorized identification.

The enabling/disabling (or locking/unlocking) process may be implemented by electrical circuit and/or software. The process may also be in form of a pop-up question allowing a user to determine whether to lock or unlock certain functionalities.

In an example, not further shown, a secondary monitoring unit is provided that provides an analogue signal that is used as a carrier signal. The information unit belongs to the secondary monitoring unit. The information unit is configured to add the data carrier signal indicative of information about the patient medical monitoring unit to the carrier signal.

In some embodiments, the interface device 26 may be configured to enable a sub-set of the at least one locked functionality based on the detected identity or identities of the hemodynamic monitoring device. For example, certain locked functionalities are allowed for hemodynamic monitoring devices from certain manufacturers. Some locked functionalities are permitted for use in certain geographic regions. Particular locked functionalities have a permissible number of uses. The interface device may thus unlock only a sub-set of the locked functionalities according to the identified information about the hemodynamic monitoring device (e.g. manufacturer, geographic regions of use, and permitted number of uses). In this way, many features of the hemodynamic monitoring systems may be customized without any further hardware changes.

The at least one locked functionality may e.g. comprise at least one of the group of: FFR measurement; pressure measurement; iFR measurement; and new functionality comprising flow, oxygenation and viscosity.

Certain functionality may be incorporated in the hemodynamic monitoring system. For example, it is possible to connect FFR catheters to the hemodynamic monitoring system for quantifying the hemodynamic severity of intracoronary lesions, providing information that can help determine if a stent is required. In this way, no additional hardware may be required to be able to carry out FFR measurements, Similarly, the iFR functionality can be switched on if the right catheter has been detected.

The mechanism can also be used to prevent double use of a patient monitoring device, e.g. a hemodynamic monitoring device (e.g. a catheter), based on e.g. serial number. Furthermore, it can be used to transmit a signal, for which the hemodynamic monitoring system does not have an input port. For example, the analogue pressure input ports of a hemodynamic monitoring system might be used for measuring parameters for which today no catheters and dedicated input ports exist, like flow, oxygenation of blood, viscosity of blood. By transmitting and identifying the information about the hemodynamic monitoring device (e.g. for measuring flow of blood), an input port that is usually a pressure input port might be used for the new parameters. The software that is used to display the signal will adapt to the new input parameter, the hardware does not have to change. For example, instead of interpreting and displaying the input signal in mmHg/mV, it could interpret it as ml/s/mV, %/mV, or St/mV. In other words, the limited numbers of standard input ports of a hemodynamic monitoring system may be extended to measure new hemodynamic parameters, thus allowing the hemodynamic monitoring system to adapt to different clinical scenarios, for example, in different countries as well as in different departments.

Although not illustrated, the hemodynamic monitoring system may be further configured to generate reports and auto-fills report fields and billing information. A user interface, e.g. a touch screen, may be provided to display and record waveforms. The user interface may also be configured to allow a user, e.g. a medical doctor or a nurse, to power the hemodynamic monitoring device by pushing a virtual "connect" button. If the information about the hemodynamic monitoring device is provided to the user e.g. in form of a pop-up question, the user may decide whether or not to unlock further functions or enable a standard input port of the hemodynamic monitoring system for measuring a new hemodynamic parameter. These features may of course be customized to each cath lab's needs.

Figure 4:
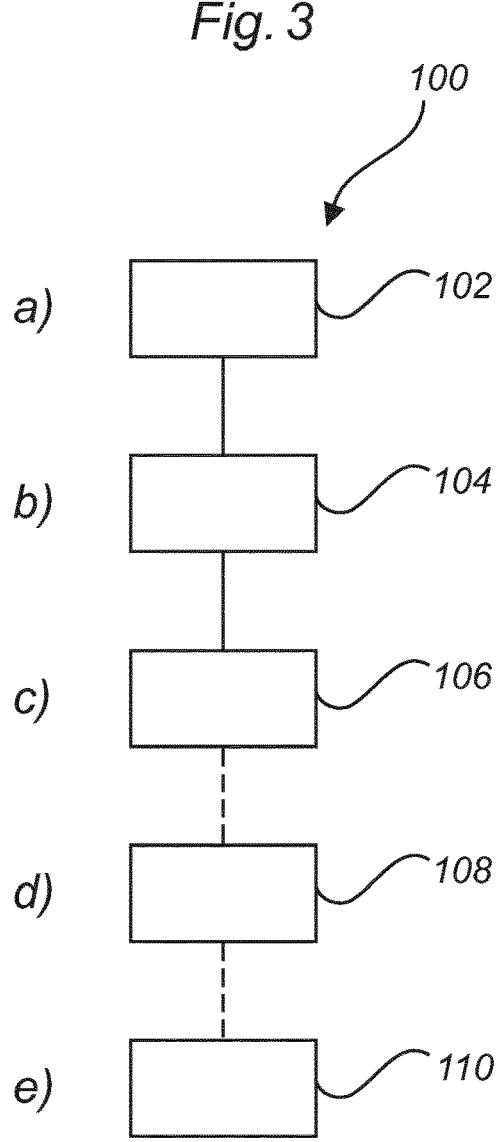
FIG. 4 shows an example of basic steps of a method for operating a hemodynamic monitoring system.

FIG. 4 shows basic steps of a method 100 for operating a patient monitoring system. The method 100 comprises the following steps:

In a first step 102, also referred to as step a), it is provided a data carrier signal indicative of information about a patient monitoring device upon connecting the patient monitoring device to a patient monitoring system;

In a second step 104, also referred to as step b), the data carrier signal is received and the information about the patient monitoring device is identified based on the received data carrier signal; and In a third step 106, also referred to as step c), the information about the hemodynamic monitoring device is considered for further steps.

The data carrier signal is provided as an analogue sequence comprising a predetermined waveform indicative of the information about the patient monitoring device.

The data carrier signal that carries data of measurements (e.g. flow, oxygenation of blood, viscosity of blood) may be sent over an input port (or channel) of the hemodynamic monitoring system that is standard used for measuring a certain parameter (e.g. pressure). In this way, the functionality of this input port (or channel) may be extended, for example, by switching on FFR or iFR, or even performing a completely new measurement like viscosity of blood.

According to a further exemplary embodiment, shown as an option in FIG. 4 (indicated by a dotted connection line), the method 100 further comprises the step of: d) detecting 108 the predetermined waveform of the analogue sequence of the received data carrier signal, and identifying the information about the patient monitoring device based on the detected predetermined waveform.

According to a further exemplary embodiment, also shown as an option in FIG. 4 (indicated by a dotted connection line), the method 100 further comprises the step of: e) enabling or disabling 110 at least one locked functionality of the patient monitoring system based on the identified information about the patient monitoring device.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A patient monitoring system, comprising:
   a patient monitoring device that includes:
      a patient medical monitor configured to perform monitoring of at least one physiological parameter of a patient and to provide measurement data of the at least one physiological parameter;
      an information processor with a memory, the information processor configured to:
         store configuration information regarding the patient monitoring device, and
         provide a data carrier signal indicative of the configuration information, and wherein the data carrier signal is provided as an analogue sequence comprising a variable waveform that is converted from the configuration information stored in the memory so as to be transmitted over an analogue interface, and
      wherein the configuration information comprises at least one of the group of:
         serial number;
         batch number;
         production data; and/or
         calibration parameters;
      a data processor configured to identify the configuration information based on the data carrier signal and to adapt functionality of the patient monitoring system based on the identified configuration information; and
      an interface device configured to receive the data carrier signal from the patient monitoring device and to provide the data carrier signal to the data processor.

2. The patient monitoring system as claimed in claim 1, wherein the information processor is configured to send data upon connection to the patient monitoring system.

3. The patient monitoring system as claimed in claim 1, wherein the patient medical monitor comprises at least one sensor configured to monitor the at least one physiological parameter; and wherein the at least one sensor is provided at an interventional device; and wherein the interventional device relates to at least one of the group of:
   a flexible elongated object to be inserted in a cavity or lumen of an anatomic structure; and/or
   a rigid or flexible elongate object to be penetrate at least a part of an anatomic structure.

4. The patient monitoring system as claimed in claim 1, wherein the patient medical monitor is provided as at least one of:
   a hemodynamic monitoring processor configured to provide at least one physiological parameter of the patient of the group of: blood pressure, blood volume, blood flow, blood flow speed, blood consistency, elasticity of a vessel, and geometry of a vessel;
   a cardiac monitor configured to provide at least one cardiac related parameter of the patient of the group of: heart rate, cardiac index, or cardiac electric activity;
   a gastroenterological monitor configured to provide at least one parameter of the patient of the group of: images inside cavities of an intestinal tract, chemical consistence of content inside a cavity of the intestinal tract, or temperature; and/or
   a neurological monitor configured to provide a signal indicative of a neurological electric activity of the patient.

5. The patient monitoring system as claimed in claim 1, wherein the patient medical monitor is provided as a catheter insertable into a vessel structure of a patient and provided as:
   a hemodynamic monitor configured to measure at least one physiological parameter of the patient of the group of: blood pressure, blood volume, blood flow, blood flow speed, blood consistency, elasticity of a vessel, and geometry of a vessel; and/or
   a cardiac monitor configured to measure at least one cardiac related parameter of the patient of the group of: heart rate, and cardiac index.

6. The patient monitoring system as claimed in claim 1, wherein the data processor is configured to detect the variable waveform of the analogue sequence of the received data carrier signal, and to identify the configuration information based on the detected variable waveform.

7. The patient monitoring system as claimed in claim 1, wherein the data processor is configured:
   to enable or disable at least one locked functionality of the patient monitoring system based on the identified configuration information; and/or
   to enable the use of a standard input port of the patient monitoring system to measure a new parameter that does not have a dedicated input port on the patient monitoring system based on the identified configuration information.

8. The patient monitoring system as claimed in claim 1, wherein a secondary monitor configured to provide an analogue signal that is used as a carrier signal;
   wherein the secondary monitor includes the information processor; and
   wherein the information processor is configured to add the data carrier signal indicative of the configuration information to the carrier signal.

9. The patient monitoring system as claimed in claim 1, wherein the data processor is configured to enable or disable at least one locked functionality of the patient monitoring system based on the identified configuration information, wherein the at least one locked functionality comprises at least one of the group of:
   fractional flow reserve measurement;
   pressure measurement;
   instant wave-free ratio measurement; and/or
   new functionality comprising flow, oxygenation and viscosity.

10. The patient monitoring system as claimed in claim 1, wherein both the measurement data and the configuration information are transmitted as analogue data.

11. A method for operating a patient monitoring system, comprising:
storing, in memory, configuration information regarding a patient monitoring device of the patient monitoring system;
providing, by the patient monitoring device, a data carrier signal indicative of the configuration information about a patient monitoring device upon connecting a hemodynamic monitor to a patient monitoring system, wherein the hemodynamic monitor is configured to perform monitoring of at least one physiological parameter of a patient to provide measurement data of the at least one physiological parameter;
receiving, by an interface device, the data carrier signal from the patient monitoring device and providing the data carrier signal to a data processor;
identifying, by the data processor, the configuration information about the patient monitoring device based on the received data carrier signal; and
adapting, by the data processor, the functionality of the patient monitoring system based on the identified configuration information,
wherein the data carrier signal is provided as an analogue sequence comprising a variable waveform that is converted from the configuration information stored in the memory so as to be transmitted over an analogue interface, and
wherein the configuration information comprises at least one of the group of:
serial number;
batch number;
production data; and/or
calibration parameters.

12. The method as claimed in claim 11, further comprising:
detecting the variable waveform of the analogue sequence of the received data carrier signal, and identifying the configuration information based on the detected variable waveform.

13. The method as claimed in claim 11, further comprising:
enabling or disabling at least one locked functionality of the patient monitoring system based on the identified configuration information; and/or
enabling the use of a standard input port of the patient monitoring system to measure a new parameter that does not have a dedicated input port on the patient monitoring system based on the identified configuration information.

14. The method as claimed in claim 11, wherein both the measurement data and the configuration information are transmitted as analogue data.

15. A non-transitory computer readable medium having stored thereon instructions that when executed by processing circuitry of a patient monitoring system cause the processing circuitry to:
store, in memory, configuration information regarding a patient monitoring device of the patient monitoring system;
provide a data carrier signal indicative of configuration information about a patient monitoring device upon connecting a hemodynamic monitor to the patient monitoring system, wherein the hemodynamic monitor is configured to perform monitoring of at least one physiological parameter of a patient to provide measurement data of the at least one physiological parameter;
receive, by an interface device, the data carrier signal and provide the data carrier signal to a data processor;
identify, by the data processor, the configuration information about the patient monitoring device based on the received data carrier signal; and
adapt, by the data processor, the functionality of the patient monitoring system based on the identified configuration information,
wherein the data carrier signal is provided as an analogue sequence comprising a variable waveform that is converted from the configuration information stored in the memory so as to be transmitted over an analogue interface, and
wherein the configuration information comprises at least one of the group of:
serial number;
batch number;
production data; and/or
calibration parameters.

16. The non-transitory computer readable medium as claimed in claim 15, further comprising instructions that when executed by the processing circuitry cause the processing circuitry to detect the variable waveform of the analogue sequence of the received data carrier signal, and identify the configuration information based on the detected variable waveform.

17. The non-transitory computer readable medium as claimed in claim 15, further comprising instructions that when executed by the processing circuitry cause the processing circuitry to:
enable or disable at least one locked functionality of the patient monitoring system based on the identified configuration information; and/or
enable the use of a standard input port of the patient monitoring system to measure a new parameter that does not have a dedicated input port on the patient monitoring system based on the identified configuration information.

18. The non-transitory computer readable medium as claimed in claim 15, wherein both the measurement data and the configuration information are transmitted as analogue data.

* * * * *